United States Patent [19]

Mochida et al.

[11] 4,440,770

[45] * Apr. 3, 1984

[54] DIURETIC, HYPOTENSIVE AND ANTIEDEMIC QUINOLINE OXIMES

[75] Inventors: Ei Mochida, Tokyo; Haruo Ohnishi, Funabashi; Kazuo Yamaguchi, Koganei; Yasuo Suzuki, Kawaguchi; Hiroshi Kosuzume, Yokohama, all of Japan

[73] Assignee: Mochida Seiyaku Kabushiki Kaisha, Tokyo, Japan

[ * ] Notice: The portion of the term of this patent subsequent to Dec. 20, 2000 has been disclaimed.

[21] Appl. No.: 281,242

[22] Filed: Jul. 7, 1981

[30] Foreign Application Priority Data

Jul. 28, 1980 [JP] Japan ................................ 55-103273
Mar. 19, 1981 [JP] Japan ................................ 56-39909

[51] Int. Cl.³ .............................................. A61K 31/47

[52] U.S. Cl. .................................. 424/258; 546/156; 546/159

[58] Field of Search ........................................ 424/258

[56] References Cited

FOREIGN PATENT DOCUMENTS 51122719  9/1980  Japan ................................ 424/258

OTHER PUBLICATIONS

Chemical Abstracts, 96:135541e, (1982) [Ohnishi, H., et al., Drugs Exp. Clin. Res. 1981, 7(6), 823–832].

Primary Examiner—Richard A. Schwartz
Attorney, Agent, or Firm—Parkhurst & Oliff

[57] ABSTRACT

A pharmaceutical composition having diuretic, hypotensive and antiedemic effects which contains a 6-halo-4-oximino-1,2,3,4-tetrahydroquinoline derivative or a salt thereof, and a method to use the above-described derivative or a salt thereof as a diuretic, hypotensive and antiedemic agent.

14 Claims, No Drawings

DIURETIC, HYPOTENSIVE AND ANTIEDEMIC QUINOLINE OXIMES

BACKGROUND OF THE INVENTION

1. Field of the Invention

This invention relates to a pharmaceutical composition having diuretic, hypotensive and antiedemic effects which contains a 6-halo-4-oximino-1,2,3,4-tetrahydroquinoline derivative or a salt thereof, and a method to use the above-described derivative or a salt thereof as a diuretic, hypotensive and antiedemic agent.

2. Description of the Prior Art

For treatment of hypertension, there have heretofore been frequently employed hypotensors having a nerve blocking effect and a vasodilative effect and diuretic agents having an effect to excrete electrolytes, especially $Na^+$ and $Cl^-$, and water.

In addition, when an edema has been generated as the result of the localized retention of water and electrolytes due to the functional depression of the liver, the heart or the like or the disorder of metabolism, diuretic agents have also been employed to excrete the retained extracellular liquid in order to prevent the occurance of secondary diseases.

Under such circumstances, it has been thought that drugs having a combination of a diuretic effect and a hypotensive effect would be more effective for treatment of hypertension and the development of such drugs has thus been sought.

However, there has heretofore been no example of a drug which has such a combination of a diuretic effect and a hypotensive effect without causing trouble for digestive organs and therefore is effective on an edema resulting from the localized retention of water or electrolytes generated by the functional depression of the liver, he heart or the like and the metabolic disorder.

We have now discovered a certain type of 6-halo-4-oximino1,2,3,4-tetrahydroquinoline derivatives have a combination of diuretic and hypotensive effects with reduced side effects and thus achieved this invention.

SUMMARY OF THE INVENTION

According to this invention there is provided a pharmaceutical composition having diuretic, hypotensive and antiedemic effects which contains a 6-halo-4-oximino-1,2,3,4-tetrahydroquinoline derivative of the formula (I):

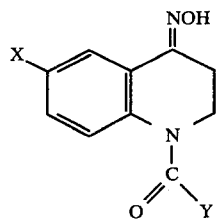

or a salt thereof, wherein X represents a halogen atom, and Y represents a straight-chain or branched-chain alkyl group having 1–4 carbon atoms, a phenyl-substituted lower alkyl group, a phenylalkenyl group, a lower alkoxy group or a lower alkyl-substituted amino group, as a main ingredient.

There is also provided according to this invention a method to use a 6-halo-4-oximino-1,2,3,4-tetrahydroquinoline derivative of the formula (I) or a salt thereof as a diuretic, hypotensive and antiedemic agent.

DESCRIPTION OF THE PREFERRED EMBODIMENT

6-Halo-4-oximino-1,2,3,4-tetrahydroquinoline derivatives of the formula (I):

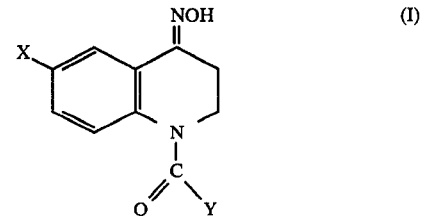

wherein X represents a halogen atom, and Y represents a straight-chain or branched-chain alkyl group having 1–4 carbon atoms, a phenyl-substituted lower alkyl group, a phenylalkenyl group, a lower alkoxy group or a lower alkyl-substituted amino group, which are the main ingredients of the pharmaceutical compositions according to this invention may be produced in general by the following steps:

A p-halogen substituted aniline is acylated with an acylating agent such as β-propiolactone, and then cyclized using an oxidizing agent such as polyphosphoric acid, to obtain a 6-halo-4-oxo-1,2,3,4-tetrahydroquinoline, which is then either reacted with a chloroformate in an inert solvent in the presence of an organic tertiary amine when Y is the above formula (I) is a lower alkoxy group or reacted with an acid anhydride or an acid halide when Y has above meanings other than an alkoxy group. Thereafter, the resulting product is converted into an oxime with hydroxylamine etc., thereby the product of this invention is obtained. (See Japanese Patent application Nos. 103272/1980, 39910/1981 and 39911/1981).

Preparation of the compounds of the formula (I) is illustrated by the following Preparations, in which "parts" is given by weight unless otherwise stated.

Preparation 1

Synthesis of 6-Bromo-4-oximino-1-acetyl-1,2,3,4-tetrahydroquinone (Compound I)

22.61 Parts of 6-bromo-4-oxo-1,2,3,4-tetrahydroquinoline and 13.3 parts of acetic anhydride were mixed and reacted with stirring at 90° C. for 3 hours. The reaction mixture was poured into 500 ml of water, and the precipitated crystals were filtered out, washed with water, and dried to obtain 23.9 parts of 6-bromo-4-oxo-1-acetyl-1,2,3,4-tetrahydroquinoline.

Then, the above compound was dissolved in 350 ml of ethanol, to which were added 14.6 parts of hydroxylamine hydrochloride and 16.1 parts of pyridine, and the reaction was continued under reflux for 2 hours. The reaction mixture was then poured into 500 ml of water, and the precipitated crystals were filtered out, washed with water, and dried to obtain 24.1 parts of 6-bromo-4-oximino-1-acetyl-1,2,3,4-tetrahydroquinoline as white crystals.

The melting point of this product, when measured by the method stipulated by the Japanese Pharmacopeia, showed 200°–202.5° C. The results of the elemental analysis of this product were as follows:

| Elemental analysis | | | | | |
|---|---|---|---|---|---|
| | C | H | Br | N | O |
| Calculated: | 46.64 | 3.89 | 28.27 | 9.89 | 11.31 |
| Found: | 46.67 | 3.84 | 28.24 | 9.92 | 11.33 |

Preparation 2

18.16 Parts of 6-chloro-4-oxo-1,2,3,4-tetrahydroquinoline, 10.3 parts of pyridine and 100 ml of dioxane were mixed and to this stirred mixture was added dropwise 12.3 parts of methyl chloroformate while maintaining the temperature at 0°–5° C. After the addition, the reaction was continued at room temperature for 5 hours.

The reaction mixture was poured into one liter of water, and the precipitated crystals were filtered out, washed with water and then with n-hexane, and dried to obtain 22.0 parts of 6-chloro-4-oxo-1-methoxycarbonyl-1,2,3,4-tetrahydroquinoline.

Then, the above compound was dissolved in 330 ml of ethanol, to which were added 15.0 parts of hydrochloride and 17.0 parts of pyridine, and the reaction was continued under reflux for 2 hours.

The reaction mixture was poured into one liter of water, and the precipitated product was filtered out, washed with water, dried, and recrystallized from ethanol to obtain 19.9 parts of 6-chloro-4-oximino-1-methoxycarbonyl-1,2,3,4-tetrahydroquinoline (CompoundX) as white crystals. The melting point of this product, when measured by the method stipulated by the Japanese Pahrmacopeia, showed 162°–163° C., and the results of the elemental analysis thereof were as follows:

| Elemental analysis | | | | |
|---|---|---|---|---|
| | O | H | Cl | N |
| Calculated: | 51.87 | 4.32 | 13.95 | 11.00 |
| Found: | 51.85 | 4.35 | 13.88 | 11.02 |

Examples of the 6-halo-4-oximino-1,2,3,4-tetrahydrouqinoline derivatives thus produced and the properties thereof are given in Table 1 below:

TABLE 1

| Comp. No. | Compound | X | Y | m.p. (°C.) | Properties |
|---|---|---|---|---|---|
| I | 6-Chloro-4-oximino-1-acetyl-1,2,3,4-tetrahydroquinoline | Cl | $CH_3$ | 214–215.5 | White crystalline powder. Sparingly soluble in water and hexane; easily soluble in methanol, acetone and chloroform. |
| II | 6-Chloro-4-oximino-1-propionyl-1,2,3,4-tetrahydroquinoline | Cl | $C_2H_5$ | 166–169 | White crystalline powder. Sparingly soluble in water and hexane; easily soluble in methanol, acetone and chloroform. |
| III | 6-Chloro-4-oximino-1-butyryl-1,2,3,4-tetrahydroquinoline | Cl | $n-C_3H_7$ | 141–142 | White crystalline powder. Sparingly soluble in water and hexane; easily soluble in methanol, acetone and chloroform. |
| IV | 6-Chloro-4-oximino-1-isobutyryl-1,2,3,4-tetrahydroquinoline | Cl | $iso-C_3H_7$ | 185–186 | White crystalline powder. Sparingly soluble in water and hexane; easily soluble in methanol, acetone and chloroform. |
| V | 6-Chloro-4-oximino-1-valeryl-1,2,3,4-tetrahydroquinoline | Cl | $n-C_4H_9$ | 118–120 | White crystalline powder. Sparingly soluble in water and hexane; easily soluble in methanol, acetone and chloroform. |
| VI | 6-Chloro-4-oximino-1-isovaleryl-1,2,3,4-tetrahydroquinoline | Cl | $iso-C_4H_9$ | 142–143 | White crystalline powder. Sparingly soluble in water and hexane; easily soluble in methanol, acetone and chloroform. |
| VII | 6-Chloro-4-oximino-1-phenylacetyl-1,2,3,4-tetrahydroquinoline | Cl | $CH_2C_6H_5$ | 181–183 | White crystalline powder. Sparingly soluble in water and hexane; easily soluble in methanol, acetone and chloroform. |
| VIII | 6-Chloro-4-oximino-1-cinnamoyl-1,2,3,4-tetrahydroquinoline | Cl | $CH=CHC_6H_5$ | 216–217 | White crystalline powder. Sparingly soluble in water and hexane; easily soluble in methanol, acetone and chloroform. |
| IX | 6-Fluoro-4-oximino-1-methoxycarbonyl-1,2,3,4-tetrahydroquinoline | F | $OCH_3$ | 145–148 | White crystals. Sparingly soluble in water and hexane; soluble in ethanol and dichloromethane. |
| X | 6-Chloro-4-oximino-1-methoxycarbonyl-1,2,3,4-tetrahydroquinoline | Cl | $OCH_3$ | 162–163 | White crystals. Sparingly soluble in water and hexane; soluble in ethanol and dichloromethane. |
| XI | 6-Bromo-4-oximino-1-methoxycarbonyl-1,2,3,4-tetrahydroquinoline | Br | $OCH_3$ | 155.5–158.5 | White crystals. Sparingly soluble in water and hexane; soluble in ethanol and dichloromethane. |
| XII | 6-Fluoro-4-oximino-1-ethoxycarbonyl-1,2,3,4-tetrahydroquinoline | F | $OC_2H_5$ | 122–124 | White crystals. Sparingly soluble in water and hexane; soluble in ethanol and dichloromethane. |
| XIII | 6-Chloro-4-oximino-1-ethoxycarbonyl-1,2,3,4-tetrahydroquinoline | Cl | $OC_2H_5$ | 112–113 | White crystals. Sparingly soluble in water and hexane; soluble in ethanol and dichloromethane. |
| XIV | 6-Bromo-4-oximino-1-acetyl-1,2,3,4-tetra- | Br | $CH_3$ | 200–202.5 | White crystals. Sparingly soluble in water and hexane; soluble in |

TABLE 1-continued

| Comp. No. | Compound | X | Y | m.p. (°C.) | Properties |
|---|---|---|---|---|---|
| | hydroquinoline | | | | ethanol and dichloromethane. |
| XV | 6-Fluoro-4-oximino-1-propionyl-1,2,3,4-tetrahydroquinoline | F | $C_2H_5$ | 126.5–128 | White crystals. Sparingly soluble in water and hexane; soluble in ethanol and dichloromethane. |
| XVI | 6-Bromo-4-oximino-1-propionyl-1,2,3,4-tetrahydroquinoline | Br | $C_2H_5$ | 151.5–152.5 | White crystals. Sparingly soluble in water and hexane; soluble in ethanol and dichloromethane. |
| XVII | 6-Bromo-4-oximino-1-isobutyryl-1,2,3,4-tetrahydroquinoline | Br | $i\text{-}C_3H_7$ | 195–197 | White crystals. Sparingly soluble in water and hexane; soluble in ethanol and dichloromethane. |
| XVIII | 6-Bromo-4-oximino-1-cinnamoyl-1,2,3,4-tetrahydroquinoline | Br | $CH{=}CHC_6H_5$ | 208.5–210.5 | White crystals. Sparingly soluble in water and hexane; soluble in ethanol and dichloromethane. |
| XIX | 6-Chloro-4-oximino-1-methylcarbamoyl-1,2,3,4-tetrahydroquinoline | Cl | $NHCH_3$ | 211–212 | White crystals. Sparingly soluble in water and hexane; soluble in ethanol and dichloromethane. |
| XX | 6-Bromo-4-oximino-1-methylcarbamoyl-1,2,3,4-tetrahydroquinoline | Br | $NHCH_3$ | 206.5 (dec.) | White crystals. Sparingly soluble in water and hexane; soluble in ethanol and dichloromethane. |
| XXI | 6-Fluoro-4-oximino-1-dimethylcarbamoyl-1,2-3,4-tetrahydroquinoline | F | $N(CH_3)_2$ | 147–149.5 | White crystals. Sparingly soluble in water and hexane; soluble in ethanol and dichloromethane. |
| XXII | 6-Chloro-4-oximino-1-dimethylcarbamoyl-1,2-3,4-tetrahydroquinoline | Cl | $N(CH_3)_2$ | 150–152 | White crystals. Sparingly soluble in water and hexane; soluble in ethanol and dichloromethane, |
| XXIII | 6-Bromo-4-oximino-1-dimethylcarbamoyl-1,2-3,4-tetrahydroquinoline | Br | $N(CH_3)_2$ | 113–115 | White crystals. Sparingly soluble in water and hexane; soluble in ethanol and dichloromethane. |

The pharmacological effect, toxicity, method for use and dosage of each of the active compounds used in the compositions of this invention are illustrated by the following Experimental Examples.

Experimental Example 1

Diuretic Effect in Rats

Wister strain male rats weighing about 200 g were starved overnight and each compound of this invention suspended in 25 ml/kg of physiological saline were administered orally to the 5 animals in each group, and the diuretic effect up to 5 hours after the administration was measured. The diuretic effect is expressed as the average urine volume (%) of the treated group divided by that of the control group. The results are given in Tables 2 and 3 below.

TABLE 2

| Diuretic Effect in Rats | | |
|---|---|---|
| Compound to be Tested | Dosage mg/kg | Diuretic Effect (%) |
| Control | | 100 |
| Compound I | 5 | 131 |
| | 10 | 186 |
| | 20 | 260 |
| Compound II | 2.5 | 253 |
| | 5 | 304 |
| | 10 | 410 |
| Compound III | 5 | 122 |
| | 10 | 172 |
| | 20 | 240 |
| Compound IV | 25 | 119 |
| | 50 | 211 |
| Compound V | 50 | 209 |
| Compound VI | 50 | 196 |
| Compound VII | 50 | 202 |
| Compound VIII | 50 | 228 |
| Furosemide | 5 | 133 |
| | 10 | 167 |
| | 20 | 304 |

TABLE 3

| Compound to be Tested | Dosage mg/kg | Diuretic Effect (%) | Compound to be Tested | Dosage mg/kg | Diuretic Effect (%) |
|---|---|---|---|---|---|
| IX | 2.5 | 251 | XV | 10 | 425 |
| | 5 | 309 | XVI | 5 | 243 |
| | 10 | 408 | | 10 | 380 |
| X | 2.5 | 188 | XVII | 50 | 173 |
| | 5 | 306 | XVIII | 50 | 203 |
| | 10 | 371 | XIX | 50 | 180 |
| XI | .5 | 152 | XX | 50 | 197 |
| | 10 | 293 | XXI | 10 | 128 |
| XII | 10 | 180 | | 20 | 209 |
| | 20 | 285 | XXII | 10 | 198 |
| XIII | 10 | 204 | | 20 | 263 |
| | 20 | 310 | XXIII | 50 | 200 |
| XIV | 20 | 234 | Furosemide | 5 | 116 |
| XV | 2.5 | 209 | | 10 | 215 |
| | 5 | 347 | | 20 | 277 |

A diuretic effect was observed in each of Compounds I to XXIII.

Experimental Example 2

Hypotensive Effect in rats with Spontaneous Hypertension (SHR)

5 male SHR's weighing 250–300 g with blood pressure of 170–190 mm Hg were used in each group. Each compound of this invention was suspended in a 5% aqueous arabic gum solution and the blood pressure was measured before administration and 2 hours after daily administration by using a plethysmorgraph. The results are given in Tables 3 and 4 below.

TABLE 4

| Hypotensive Effect in SHR's | | | | | |
|---|---|---|---|---|---|
| | | Blood Pressure (mm Hg) | | | |
| Compound to be Tested | Dosage mg/kg | Before Administration | After 2 days | After 4 days | After 8 days |
| Control | | 180 | 177 | 178 | 175 |

TABLE 4-continued

Hypotensive Effect in SHR's

| Compound to be Tested | Dosage mg/kg | Blood Pressure (mm Hg) | | | |
|---|---|---|---|---|---|
| | | Before Administration | After 2 days | After 4 days | After 8 days |
| I | 50 | 178 | 170 | 167 | 164 |
| II | 20 | 182 | 167 | 161 | 158 |
| III | 50 | 179 | 166 | 165 | 157 |
| IV | 100 | 182 | 172 | 169 | 162 |
| V | 200 | 181 | 169 | 165 | 166 |
| VI | 200 | 179 | 168 | 167 | 163 |
| VII | 200 | 179 | 172 | 168 | 168 |
| VIII | 100 | 181 | 169 | 164 | 159 |

TABLE 5

| Compound to be Tested | Dosage mg/kg | Blood Pressure (mm Hg) | | | |
|---|---|---|---|---|---|
| | | Before Administration | After 2 days | After 4 days | After 8 days |
| Control | | 181 | 179 | 182 | 180 |
| IX | 20 | 181 | 164 | 158 | 157 |
| X | 20 | 180 | 169 | 158 | 155 |
| XI | 20 | 181 | 176 | 171 | 165 |
| XII | 50 | 179 | 174 | 170 | 160 |
| XIII | 50 | 182 | 170 | 165 | 162 |
| XIV | 50 | 180 | 175 | 169 | 163 |
| XV | 20 | 181 | 166 | 159 | 154 |
| XVI | 20 | 183 | 171 | 163 | 158 |
| XVII | 100 | 181 | 176 | 178 | 176 |
| XVIII | 100 | 182 | 177 | 175 | 167 |
| XIX | 100 | 180 | 175 | 174 | 170 |
| XX | 100 | 179 | 173 | 173 | 167 |
| XXI | 50 | 183 | 175 | 167 | 166 |
| XXII | 50 | 181 | 170 | 169 | 163 |
| XXIII | 100 | 180 | 172 | 166 | 167 |

Experiment Example 3

Inhibition for Carrageenin-Induced Foot Edema in Rats

10 Wister strain male rats weighing about 120 g were used in each group. Each compound of this invention was suspended in a 5% aqueous arabic gum solution and administered orally to the animals. One hour after the administration, 0.1 ml of a 1% solution of carrageenin in physiological saline as a phlogistic agent was subcutaneously injected into the right hind paw of the rats which had been shaven previously. The volume of the right hind paw was measured before the administration of the phlogistic agent and 3 hours after the administration. The intensity of edema expressed as percent increase in the foot volume was calculated from the aqueous (1) and the percent inhibition of edema was calculated from the equation (2).

Percent Edema (%) = Equation (1)

$$\left[ \frac{\text{Foot Volume 3 hrs. after Administration (ml)}}{\text{Foot Volume before Administration (ml)}} - 1 \right] \times 100$$

Percent Inhibition of Edema (%) = Equation (2)

$$\left[ 1 - \frac{\text{Percent Edema in Treated Group (\%)}}{\text{Percent Edema in Control Group (\%)}} \right] \times 100$$

The effective dosage of each compound for inhibiting edema was expressed as $ED_{30}$ (mg/kg) by calculating the dosage for 30% inhibition from the percent inhibition of edema according to the probit method. The results are given in Tables 6 and 7 below.

TABLE 6

Inhibition for Carrageenin-Induced Foot Edema in Rats

| Compound | $ED_{30}$ (mg/kg) |
|---|---|
| I | 39 |
| II | 8.8 |
| III | 33 |
| IV | 87 |
| V | 140 |
| VI | 105 |
| VII | 140 |
| VIII | 44 |
| Phenylbutazone | 65 |

TABLE 7

| Compound to be Tested | $ED_{30}$ (mg/kg) | Compound to be Tested | $ED_{30}$ (mg/kg) |
|---|---|---|---|
| IX | 22 | XVII | 102 |
| X | 14 | XVIII | 133 |
| XI | 83 | XIX | 62 |
| XII | 86 | XX | 95 |
| XIII | 49 | XXI | 141 |
| XIV | 182 | XXII | 34 |
| XV | 9.3 | XXIII | 51 |
| XVI | 16 | Phenylbutazone | 63 |

The inhibitory effect for carrageenin-induced foot edema in rats was observed in each of the Compounds I–XXIII.

Experimental Example 4

Acute Oral Toxicity in Mice 10 ddY Strain male mice weighing about 20 g were used in each group. Each compound of this invention was suspended in a 5% aqueous gum arabic solution and administered orally. The mortality rate (%) was determined from the number of dead animals 7 days after the administration, and the dosage corresponding to 50% mortality was calculated and expressed as $LD_{50}$ (mg/kg). The results are given in Table 8 below.

TABLE 8

Acute Oral Toxicity in Mice

| Compound to be Tested | $LD_{50}$ (mg/kg) |
|---|---|
| I | >5,000 |
| II | 3,488 |
| III | >5,000 |
| IV | >5,000 |
| V | >5,000 |
| VI | >5,000 |
| VII | >5,000 |
| VIII | >5,000 |
| IX | >5,000 |
| X | 4,470 |
| XI | >5,000 |
| XII | >5,000 |
| XIII | >5,000 |
| XIV | >5,000 |
| XV | 3,440 |
| XVI | 4,710 |
| XVII | >5,000 |
| XVIII | >5,000 |
| XIX | >5,000 |
| XX | >5,000 |
| XXI | >5,000 |
| XXII | >5,000 |
| XXIII | >5,000 |

All of the LD$_{50}$ values of Compounds I–XXIII are greater than the levels which show a pharmaceutical effect and thus the compounds are of sufficient safety.

As evident from the above-described experimental examples, all of the compounds of the formula (I) according to this invention have remarkable diuretic and antiedemic effects as well as a mild hypotensive effect. Further, these compounds are of very low toxicity and are adequately safe at the dosage at which a pharmaceutical effect is manifested. Therefore, the compounds of this invention are not only useful for the treatment of hypertension but also extremely useful for the treatment of edema resulting from the localized retention of water and electrolytes generated by the functional depression of the liver, the heart or the like or the metabolic disorder.

While the compounds of this invention are usually administered orally or intrarectally, they can also be administered as an injectable composition or as a topical composition. The dose of each compound for a human adult is given in Table 9, but this may be out of the exemplified range as appropriate depending on the severity of the disease or the administration route, and on therapeutical demand.

TABLE 9

| Compound | Dose for Treating Human Adults Dose (mg/day) | Compound | Dose (mg/day) |
| --- | --- | --- | --- |
| I | 20–2,000 | V | 80–6,000 |
| II | 5–1,000 | VI | 80–6,000 |
| III | 20–2,000 | VII | 80–6,000 |
| IV | 25–2,500 | VIII | 40–4,000 |
| IX | 20–2,000 | XVII | 80–6,000 |
| X | 10–2,000 | XVIII | 80–6,000 |
| XI | 30–2,500 | XIX | 50–4,500 |
| XII | 30–2,500 | XX | 50–4,500 |
| XIII | 30–2,500 | XXI | 80–6,000 |
| XIV | 40–4,000 | XXII | 20–2,000 |
| XV | 5–1,000 | XXIII | 40–4,000 |
| XVI | 10–2,000 | | |

Generally speaking, peroral or intrarectal administration of 0.02–200 mg, in particular 0.1–100 mg of the compound per day per one kg of the patient's body weight would be desirable for the purpose of achieving the expected effect. In the general case of an adult a daily administration of 1 to 10 units of a composition containing 5–600 mg of the composition according to the present invention will suffice. For injection, about the same to 1/10 of the above dosage will have approximately the same effect.

The compounds of this invention may be formulated into pharmaceutical preparations in a conventional manner with conventional additives, i.e. a pharmaceutical carrier, base material or excipient.

As the pharmaceutical carrier or the base material, there may be employed lactose, mannitol, corn starch, potato starch etc. Examples of the excipient which can be used are crystalline cellulose, cellulose derivatives, gum arabic, corn starch, gelatin etec. In addition, a disintegrant such as calcium carboxymethyl cellulose and a lubricant such as talc, magnesium stearate etec. as well as polyvinylalcohol etc. may also be employed as the additive. As the liquid carrier when formulated into an injectable composition, there may be employed distilled water for injection, physiological saline, aqueous dextrose, vegetable oils for injection, glycols such as propylene glycol, polyethylene glycol etc. and so forth.

Preferred oral compositions are in the form of capsules, tablets, powders and oral liquid preparations, and preferred intrarectal compositions are rectal suppositories. The injectable composition is preferably a suspension containing a pharmaceutically acceptable dispersing agent such as Tween 80, aqueous gum arabic etc., and the topical composition is preferably presented as an ointment The amount of the active compound of the formula (I) in the composition is 1–99.9% by weight, preferably 1–99.0% by weight and especially 5–70% by weight.

This invention is more particularly described by the following examples.

EXAMPLE 1

Capsules

| Compound I | 500 g |
| --- | --- |
| Lactose | 485 g |
| Magnesium stearate | 15 g |
| | 1000 g |

The above components are weighed respectively and mixed together uniformly. Each of 500 mg of the mixed powder is filled into hard gelatin capsules No. 1 to prepare capsules.

EXAMPLE 2

Tablets

| Compound XV | 500 g |
| --- | --- |
| Lactose | 320 g |
| Potato starch | 150 g |
| Polyvinylalcohol | 15 g |
| Magnesium stearate | 15 g |
| | 1000 g |

The above components are weighed respectively, and Compound XV, lactose and potato starch are mixed together uniformly. To this mixture is added an aqueous solution of polyvinylalcohol, and granules are prepared by a wet pelletization method. The granules are dried, magnesium stearate is added and compressed on a tabletting machine to prepare tablets weighing 200 mg each.

EXAMPLE 3

Powder

| Compound XIII | 100 g |
| --- | --- |
| Lactose | 890 g |
| Magnesium stearate | 10 g |
| | 1000 g |

The above components are weighed respectively, and mixed together uniformly, to prepare a 10% powder.

EXAMPLE 4

Suppository

| Compound XIII | 100 g |
| --- | --- |
| Polyethylene glycol 1500 | 180 g |
| Polyethylene glycol 4000 | 720 g |
| | 1000 g |

What is claimed is:

1. A pharmaceutical composition containing a diuretic, hypotensive and antiedemic effective amount of a 6-halo-4-oximino-1,2,3,4-tetrahydroquinoline derivative of the formula (I):

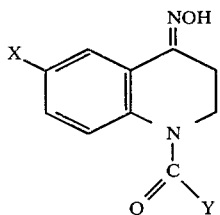

(I)

or a salt thereof, wherein X represents a halogen atom, and Y represents a straight-chain or branched-chain alkyl group having 1-4 carbon atoms, a phenyl-substituted lower alkyl group, a phenylalkenyl group, a lower alkoxy group or a lower alkyl-substituted amino group, as an active ingredient together with a conventional pharmaceutically acceptable additive.

2. The pharmaceutical composition according to claim 1 which contains 1.0-99.9% by weight of the active ingredient and 99.0-0.1% by weight of the additive.

3. The pharmaceutical composition according to claim 1 which contains 5-70% by weight of the active ingredient and 95-30% by weight of the additive.

4. The pharmaceutical composition according to claim 1, 2 or 3 in which the active ingredient is selected from the group consisting of
6-chloro-4-oximino-1-acetyl-1,2,3,4-tetrahydroquinoline,
6-chloro-4-oximino-1-propionyl-1,2,3,4-tetrahydroquinoline,
6-chloro-4-oximino-1-butyryl-1,2,3,4-tetrahydroquinoline,
6-chloro-4-oximino-1-isobutyryl-1,2,3,4-tetrahydroquinoline,
6-chloro-4-oximino-1-valeryl-1,2,3,4-tetrahydroquinoline,
6-chloro-4-oximino-1-isovaleryl-1,2,3,4-tetrahydroquinoline,
6-chloro-4-oximino-1-phenylacetyl-1,2,3,4-tetrahydroquinoline,
6-chloro-4-oximino-1-cinnamoyl-1,2,3,4-tetrahydroquinoline,
6-fluoro-4-oximino-1-methoxycarbonyl-1,2,3,4-tetrahydroquinoline,
6-chloro-4-oximino-1-methoxycarbonyl-1,2,3,4-tetrahydroquinoline,
6-bromo-4-oximino-1-methoxycarbonyl-1,2,3,4-tetrahydroquinoline,
6-fluoro-4-oximino-1-ethoxycarbonyl-1,2,3,4-tetrahydroquinoline,
6-chloro-4-oximino-1-ethoxycarbonyl-1,2,3,4-tetrahydroquinoline,
6-bromo-4-oximino-1-acetyl-1,2,3,4-tetrahydroquinoline,
6-fluoro-4-oximino-1-propionyl-1,2,3,4-tetrahydroquinoline,
6-bromo-4-oximino-1-propionyl-1,2,3,4-tetrahydroquinoline,
6-bromo-4-oximino-1-isobutyryl-1,2,3,4-tetrahydroquinoline,
6-bromo-4-oximino-1-cinnamoyl-1,2,3,4-tetrahydroquinoline,
6-choro-4-oximino-1-methylcarbamoyl-1,2,3,4-tetrahydroquinoline,
6-bromo-4-oximino-1-methylcarbamoyl-1,2,3,4-tetrahydroquinoline.
6-fluoro-4-oximino-1-dimethylcarbamoyl-1,2,3,4-tetrahydroquinoline,
6-chloro-4-oximino-1-dimethylcarbamoyl-1,2,3,4-tetrahydroquinoline, and
6-bromo-4-oximino-1-dimethylcarbamoyl-1,2,3,4-tetrahydroquinoline.

5. The pharmaceutical composition according to any of claims 1-4 in which the additive is selected from the group consisting of Tween 80, arabic gum, lactose, magnesium stearate, potato starch, polyvinylalcohol and polyethylene glycol.

6. The pharmaceutical composition according to any of claims 1-5 which is in the form selected from the group consisting of an oral dosage form, a rectal dosage form, an injectable form and a topical application form.

7. A method for treating a disease selected from the group consisting of hypertension and edema which comprises administering to a human body needing treatment for such a disease an effective amount of a 6-halo-4-oximino-1,2,3,4-tetrahydroquinoline derivative of the formula (I):

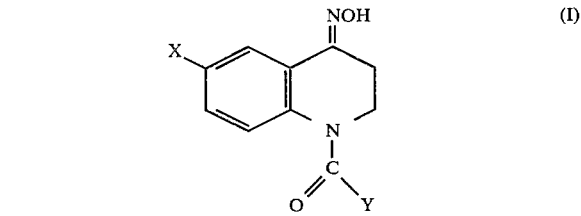

(I)

or a pharmaceutically acceptable salt thereof, wherein X represents a halogen atom, and Y represents a straight-chain or branched-chain alkyl group having 1-4 carbon atoms, a phenyl-substituted lower alkyl group, a phenylalkenyl group, a lower alkoxy group or a lower alkyl-substituted amino group.

8. The method according to claim 7 in which the daily dose of the compound of the formula (I) or the salt thereof is in the range of 1 mg to 10 g.

9. The method according to claim 8 in which the daily dose of the compound of the formula (I) or a salt thereof is in the range of 5 mg to 6 g.

10. The method according to claim 7, 8 or 9 in which the compound of the formula (I) or a salt thereof is administered orally, intrarectally, by injection or topically.

11. A method for treating a disease selected from the group consisting of hypertension and edema which comprises administering to a human body needing treatment for such a disease an effective amount of a composition comprising a carrier and a compound of the formula (I)

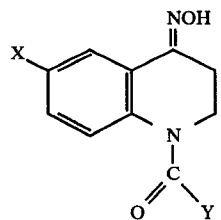 (I)

wherein X represents a halogen and Y represents a straight-chain or branched chain alkyl having 1-4 carbon atoms, a phenyl-substituted lower alkyl, a phenylalkenyl, a lower alkoxy or a lower alkyl-substituted amino group, or a pharmaceutically acceptable salt thereof.

12. The method according to claim 11 in which the daily dose of the compound of the formula (I) or the salt thereof is in the range of 1 mg to 10 g.

13. The method according to claim 12 in which the daily dose of the compound of the formula (I) or a salt thereof is in the range of 5 mg to 6 g.

14. The method according to claim 11, 12 or 13 in which the compound of the formula (I) or a salt thereof is administered orally, intrarectally, by injection or topically.

* * * * *

UNITED STATES PATENT AND TRADEMARK OFFICE
CERTIFICATE OF CORRECTION

PATENT NO. : 4,440,770
DATED : April 3, 1984
INVENTOR(S) : Mochida et al

It is certified that error appears in the above—identified patent and that said Letters Patent is hereby corrected as shown below:

In the first column of the cover page, under the heading "Inventors", the following corrections should appear:

change "Yokohama," to --Yokohama; Susumu Jinbo, Tokyo; Shoichi Kohno, Tokyo; Koichi Kashima, Tokyo,--.

In the first column of the cover page, under the heading "Foreign Application Priority Data", the following insertion should be made:

```
--July 28, 1980 [JP]  Japan...............55-103272
  March 19, 1981 [JP] Japan...............56-39910
  March 19, 1981 [JP] Japan...............56-39911--
```

Signed and Sealed this

Eighteenth Day of September 1984

[SEAL]

Attest:

GERALD J. MOSSINGHOFF

Attesting Officer

Commissioner of Patents and Trademarks